(12) United States Patent
Auh et al.

(10) Patent No.: US 8,491,942 B2
(45) Date of Patent: Jul. 23, 2013

(54) PREVENTING OR TREATING PERIODONTAL DISEASES BY HERBAL EXTRACT

(75) Inventors: Jin Auh, Seoul (KR); Chang-Kyun Han, Seoul (KR); Young-June Shin, Gimhae (KR); Hyo-Jin Moon, Suwon (KR); Jong-Wook Lee, Suwon (KR); Tae-Hoo Yi, Seoul (KR); Kang-Jin Lee, Seoul (KR); Kang-Hyun Leem, Seoul (KR)

(73) Assignee: Ahn-Gook Pharmaceutical Co., Ltd., Seoul (KR)

( * ) Notice: Subject to any disclaimer, the term of this patent is extended or adjusted under 35 U.S.C. 154(b) by 0 days.

(21) Appl. No.: 13/394,957

(22) PCT Filed: Oct. 15, 2010

(86) PCT No.: PCT/KR2010/007097
§ 371 (c)(1),
(2), (4) Date: Mar. 8, 2012

(87) PCT Pub. No.: WO2011/046395
PCT Pub. Date: Apr. 21, 2011

(65) Prior Publication Data
US 2012/0195986 A1 Aug. 2, 2012

(30) Foreign Application Priority Data
Oct. 16, 2009 (KR) ........................ 10-2009-0098617

(51) Int. Cl.
*A01N 65/00* (2009.01)
(52) U.S. Cl.
USPC ........................................................ 424/725

(58) Field of Classification Search
None
See application file for complete search history.

(56) References Cited

U.S. PATENT DOCUMENTS
2003/0228379 A1    12/2003    Shi et al.

FOREIGN PATENT DOCUMENTS

| CN | 1654056 | 8/2005 |
|---|---|---|
| CN | 101474266 | 8/2009 |
| KR | 10-2000-0030252 | 6/2000 |
| KR | 10-2001-0002311 | 1/2001 |
| KR | 10-2009-0110401 | 10/2009 |
| KR | 10-0991857 | 10/2010 |

OTHER PUBLICATIONS

Hideharu Otsuka, "Usefulness of Crevicular Coptis Rhizoma therapy for periodontal disease", Journal of Japanese Association of Periodontalogy, vol. 42, No. 2, pp. 82-91, Apr. 1, 2000.
Shyh-Jye Lin et al., "In vitro anti-microbial and in vivo cytokine modulaling effects of different prepared Chinese herbal medicines", Food and Chemical Toxicology, vol. 44, No. 12, pp. 2078-2085, Dec. 2006.
Chinese commercial herbal medicine book, p. 825, Harbin Publisher, published on Aug. 31, 1990.

*Primary Examiner* — Michael Meller
(74) *Attorney, Agent, or Firm* — Lexyoume IP Meister, PLLC.

(57) ABSTRACT

A use an extract of *Coptidis Rhizoma* or a combined extract of *Coptidis Rhizoma* and *Pharbitidis Semen* as an active ingredient for preventing and/or treating periodontal disease is provided. The extract of *Coptidis Rhizoma* or a combined extract of *Coptidis Rhizoma* and *Pharbitidis Semen* has activities to stimulate anti-inflammation, osteoblast differentiation and alveolar bone regeneration, and to prevent the alveolar bone destruction, thereby being effective for the prevention and/or treatment of periodontal disease.

7 Claims, 5 Drawing Sheets

CT-3D image

CT-2D image

Figure 5

PREVENTING OR TREATING PERIODONTAL DISEASES BY HERBAL EXTRACT

FIELD OF THE INVENTION

A composition for preventing and/or treating periodontal disease, which comprises an extract of *Coptidis Rhizoma* or a combined extract of *Coptidis Rhizoma* and *Pharbitidis Semen* as an active ingredient; a use of an extract of *Coptidis Rhizoma* or a combined extract of *Coptidis Rhizoma* and *Pharbitidis Semen* as an active ingredient for the prevention and/or treatment of periodontal disease; and a method of the prevention and/or treatment of periodontal disease by administering an extract of *Coptidis Rhizoma* or a combined extract of *Coptidis Rhizoma* and *Pharbitidis Semen*, are provided. The extract of *Coptidis Rhizoma* or a combined extract of *Coptidis Rhizoma* and *Pharbitidis Semen* has activities to stimulate anti-inflammation, osteoblast differentiation and alveolar bone regeneration, and to prevent the alveolar bone destruction.

BACKGROUND OF THE INVENTION

The periodontal tissue is composed of alveolar bone, periodontal ligament and gingiva (gum). The alveolar bone is attached firmly to the basal bone of the jaw bone, and is the 2-3 mm region adjacent to the dental root, but usually is all of the scleroid tissue including the above alveolar bone. Alveolar bone lowers down as human ages, sometimes exposing the root of the tooth. Also loss of a tooth can cause the loss of alveolar bone. The alveolar bone and tooth are attached by periodontal ligament, which has undifferentiated mesenchymal cells, with an average thickness of 0.2 mm. Alveolar bone buffers and distributes the force when chewing food, and sends the sensation of tooth to the alveolar bone by way of periodontal ligaments. Also, the periodontal ligament is a layer with undifferentiated mesenchymal cells and is structured for bone remodeling and adapted to pressure without losing the structure and function of whole fiber. The undifferentiated mesenchymal cells inside the periodontal ligament move to adjacent tissues. The cells move to the alveolar bone for bone remodeling and to teeth for holding them tight by forming collagen fiber continuously.

Gingiva is a part of supporting tissues that can be seen from outside in the mouth, and usually is a starting point of the disease (gingivitis). When the disease spreads into the supporting tissues, root surface and the periodontal ligament attached to the bone tissue around the tooth are destroyed causing subsequent destruction of alveolar bone to cause periodontal disease.

Periodontal disease is one of the most frequently occurring diseases in the oral cavity alongside with dental caries with the clinical symptoms of gingival bleeding, glossoncus, formation of periodontal pocket, loss of attached gingiva, alveolar bone destruction and ozostomia and a major cause of tooth loss (Ali, R. W. et al., *J. Clin. Periodontol.* 1997, 24, 830-835; Socransky, S. S. et al., *J. Clin. Periodontol.* 1998, 15, 440-444). Periodontal disease is one of the generally occurring chronic disease caused by inflammation, and about 10 to 60% of adults have the disease with various diagnostic stages (Xiong, X. et al., BJOG. 2006, 113, 135-143; Albandar, J. M. and T. E. Rams, *Periodontol.* 2000, 2002, 29, 7-10).

The types of periodontal disease include gingivitis with inflammation in the soft tissue and gingiva and periodontitis with destruction of supporting tissue of the periodontal ligament, alveolar bone, caries of cementum and soft tissues (Kinane D. F., *Periodontol.* 2000, 2001, 25, 8-20). Periodontal disease, which can incur the tooth loss, is a disease by bacterial infection and is caused by the microorganisms and the their secretion inducing inflammation coexisting in the biofilms called dental plaque (Feng, Z., and A. Weinberg, *Periodontol.* 2000, 2006, 40, 50-76).

As people age, periodontal disease such as periodontitis or alveolar osteochondrodyslpasia can be caused when the alveolar bones weakens by congenital or acquired reasons. The above alveolar osteochondrodyslpasia can cause tooth loss due to alveolar osteoporosis, alveolar osteomalacia, and alveolar bone loss. Alveolar bone maintains itself by remodeling including osteogenesis by osteoblast and osteolysis by osteoclast. These metabolism is controlled by the hormonal system and local factors, and alveolar osteochondrodyslpasia such as alveolar osteoporosis can be caused when the bone mass decreased below limitations by excessive osteolysis than osteogenesis. Osteoblast can help osteogenesis by precipitating the organic material in the bone, osteoid, which is composed of type 1 collagen, osteocalcin, osteonectin and sialoprotein. Formed osteoid later go through mineralization in which the osteoblast induce the mineralization of forming hydroxyapatite, a crystallite of calcium phosphate, to be precipitated to osteoid.

There has been increasing reports showing the relationship between periodontal disease and systemic diseases including arteriosclerosis, heart attack, stroke, diabetes and pregnancy complications (Desvarieux, M. et al., *Circulation*, 2005, 111, 576-582; Offenbacher, S. et al., *J. Periodontol.*, 1996, 67, 1103-1113; Garcia, R. I. et al., *Periodontol.* 2000, 2001, 25, 21-36; Champagne, C. M. et al., *J. Int. Acad. Periodontol.*, 2000, 2, 9-13; Paquette, D. W., *J. Int., Acad. Periodontol.*, 2002, 4, 101-119). And pregnancy complications related to periodontal diseases are reported to be premature birth, low birth weight, miscarriage and preeclampsia (McCormick, M. C., *N. Engl. J. Med.*, 1985, 312, 82-90; Shennan, A. H., *BMJ*, 2003, 327, 604-618). Therefore, it is most important to develop effective drugs for periodontal disease since it is a big threat for public health.

Improvement of oral hygiene, non-surgical and surgical treatments (scaling, root planing, curettage and alveolar tissue regeneration), and the like are used for the treatment of periodontal disease. Since surgical method, the most effective treatment, is cumbersome due to hospital visitation and has limitations of being done after development of the disease, periodontal disease becomes a chronic disease. Antibiotics or local sustained release formulations have been used as additive therapy, but the drugs go to unnecessary parts of the body causing side-effects such as resistance. Recently resistant microorganism of periodontal disease has been identified.

To overcome the limitations of the above surgical therapy and use of antibiotics and to improve the prevention and therapeutic effects, development of new drug with anti-inflammatory activity and ability to recover the alveolar tissues from destruction and loss is needed.

DETAILED DESCRIPTION OF THE INVENTION

Technical Problem

As the results of studies for developing treatment of periodontal disease, the present inventors have identified that an extract of *Coptidis Rhizoma* or a mixture of the extracts of *Coptidis Rhizoma* and *Pharbitidis semen* has excellent anti-inflammatory activity, osteoblast differentiation activity and activity for alveolar bone regeneration, and activity for decreasing the alveolar bone destruction, and have completed the present invention by confirming that the a combined extract of *Coptidis Rhizoma* and *Pharbitidis semen* especially have a higher pharmacological synergistic effect for the above activities than *Coptidis Rhizoma* extract alone or *Pharbitidis Semen* extract alone.

Therefore the object of the present invention is to provide an extract of *Coptidis Rhizoma* and a mixture with an optimal mixing ratio between of *Coptidis Rhizoma* extract and *Pharbitidis Semen* extract, to have the most effective pharmacological synergistic effect.

Technical Solution

The present invention relates to a composition, a use, and a method for preventing and/or treating periodontal disease, using an extract of *Coptidis Rhizoma* or a combined extract of *Coptidis Rhizoma* and *Pharbitidis Semen* as an active ingredient. In the present invention, the extract of *Coptidis Rhizoma* alone and/or a combined extract of *Coptidis Rhizoma* and *Pharbitidis Semen* has activities to stimulate anti-inflammation, osteoblast differentiation and alveolar bone regeneration, and to prevent the alveolar bone destruction.

The present inventors have completed the present invention by confirming that the combined extract of *Coptidis Rhizoma* and *Pharbitidis Semen* has a higher activities of increasing anti-inflammatory activity, osteoblast differentiation and alveolar bone regeneration, and of decreasing the alveolar bone destruction than *Coptidis Rhizoma* extract alone or *Pharbitidis Semen* extract alone and by identifying the optimum ratio between *Coptidis Rhizoma* extract and *Pharbitidis Semen* extract showing the highest synergistic effect.

*Coptidis Rhizoma* is a perennial herb belonging to Ranunculaceae family with antimicrobial activity, antihypertensive activity and anti-inflammatory activity. In oriental medicine, *Coptidis Rhizoma* is used as stomachic and modulators for central nervous system, uterus, bladder, trachea and nervous systems. It is known to contain alkaloids such as berberine and magnoflorine, and the like, as main pharmacological components (Chung and Shin, Pictured dictionary of herbal medicines, 490-493, 1990).

*Pharbitidis Semen* is a seed of *Pharbitis nil* Choisy or *Pharbitis purpurea* Voigt of Convolvulaceae family. *Pharbitis nil* Choisy is originally from tropical Asia such as India with 256 variants, and black and white seeds are called black and white Pharbitis seeds, respectively. When broken, *Pharbitidis Semen* has a faint odor, irritant, bitter in taste, cold characteristic and poisonous. *Pharbitidis Semen* causes diarrhea and has diuretic action and can be used for edema and ascites due to chronic pyelonephritis and liver cirrhosis. It is effective in chronic cough and asthma and also used for constipation and removal of parasites. Pharmacological activities include peristaltic movement to cause diarrhea. *Pharbitidis Semen* contains about 2% of pharbitin, resin glycoside, and 11% of fatty acids including olein, palmitin and stearin (Moon, Composition and use of herbs, p589, 1984). In the mean time, researcher among the present invention has applied a patent for the use of *Pharbitidis Semen* in the treatment of periodontal disease by elucidating the activity for inhibition of NO formation and activation of alkaline phosphates (KR 10-2008-0035877, a pharmacological composition for the prevention and treatment of periodontal disease containing *Pharbitidis Semen* extract as active ingredients).

As describe above, the combined extract of *Coptidis Rhizoma* and *Pharbitidis Semen* as well as the extract of *Coptidis Rhizoma* alone have anti-inflammatory activity and activity for the osteoblast differentiation in the present invention, and especially the combined extract of *Coptidis Rhizoma* and *Pharbitidis Semen* has higher activities than *Coptidis Rhizoma* extract alone or *Pharbitidis Semen* extract alone. The object of the present invention is to provide the mixture and its preparation method with optimal composition ratio with the higher pharmacological synergistic effect.

First of all, the present invention relates to an activity of an extract of *Coptidis Rhizoma* or a combined extract of *Coptidis Rhizoma* and *Pharbitidis Semen* for stimulating anti-inflammation, osteoblast differentiation and alveolar bone regeneration, and preventing the alveolar bone destruction.

More specifically, one embodiment of the present invention provides a composition for preventing and/or treating periodontal disease, which comprises an extract of *Coptidis Rhizoma* or a combined extract of *Coptidis Rhizoma* and *Pharbitidis Semen* as an active ingredient. Another embodiment provides a use of an extract of *Coptidis Rhizoma* or a combined extract of *Coptidis Rhizoma* and *Pharbitidis Semen* as an active ingredient for the prevention and/or treatment of periodontal disease, or for preparing an agent for the prevention and/or treatment of periodontal disease. Still another embodiment provides a method of the prevention and/or treatment of periodontal disease by administering an extract of *Coptidis Rhizoma* or a combined extract of *Coptidis Rhizoma* and *Pharbitidis Semen*. The method of the prevention and/or treatment of periodontal disease may comprise the step of administering an extract of *Coptidis Rhizoma* or a combined extract of *Coptidis Rhizoma* and *Pharbitidis Semen* as active ingredients to a patient in need of the prevention or treatment of periodontal disease, and optionally comprises the step of identifying the patient who needs the prevention or treatment of periodontal disease or suffers from periodontal disease, before the step of administering.

In the present invention, the term 'combined extract of *Coptidis Rhizoma* and *Pharbitidis Semen*' is intended to refer to both the mixture of *Coptidis Rhizoma* extract and *Pharbitidis Semen* extract each obtained by extracting *Coptidis Rhizoma* and *Pharbitidis Semen*, respectively, and the extract obtained from the mixture of *Coptidis Rhizoma* and *Pharbitidis Semen*. The term 'extract' as used herein means a crude extract, and/or a specific solvent-soluble extract or fraction of the crude extract, and it may be in the form of a solution, concentrate, powder, and the like.

One embodiment of the present invention may be characterized by having synergistic effect in the anti-inflammatory and osteoblast differentiation activities by using combined extract of *Coptidis Rhizoma* and *Pharbitidis Semen* when compared to *Coptidis Rhizoma* extract alone or *Pharbitidis Semen* extract alone. In order to maximize the synergistic effects in the anti-inflammatory and osteoblast differentiation activities, the weight ratio of the dry matter between *Coptidis Rhizoma* extract and *Pharbitidis Semen* extract in the above combined mixture is 0.5:1 to 30:1 (weight of *Coptidis Rhizoma* extract: weight of *Pharbitidis Semen* extract), preferably 1:1 to 25:1, more preferably 2.5:1 to 20:1, and even more preferably 7.5:1 to 15:1. The above 'dry matter' refers to the matter without the solvent used for the extraction.

In a preferred embodiment of the present invention, the combined extract according to the present invention may be a mixture of *Coptidis Rhizoma* extract and *Pharbitidis Semen* extract.

The *Coptidis Rhizoma* extract may be a crude extract obtained by extracting *Coptidis Rhizoma*, preferably the rhizome part thereof with one or more solvents selected from the group consisting of water and linear or branched alcohol having 1 to 4 carbons, or a solvent-soluble extract obtained by adding at least one aqueous solution of linear or branched alcohol having 1 to 6 carbons, preferably propyl alcohol aqueous solution, isopropyl alcohol aqueous solution and water-saturated butyl alcohol to the crude extract.

The *Pharbitidis Semen* extract may be a crude extract obtained by extracting the powdered *Pharbitidis Semen* with one or more solvents selected from the group consisting of water and linear or branched alcohol having 1 to 4 carbons, or a solvent-soluble extract obtained by adding one or more solvents selected from the group consisting of an aqueous solution of linear or branched alcohol having 1 to 6 carbons, preferably propyl alcohol aqueous solution, isopropyl alcohol aqueous solution and water-saturated butyl alcohol to the crude extract.

In a preferable embodiment, the solvent used for preparing the crude extract of *Coptidis Rhizoma* or *Pharbitidis Semen* may be one or more selected from the group consisting of water, 10 to 70% (v/v), preferably 20 to 60% (v/v), more preferably 25 to 55% (v/v) of linear or branched alcohol having 1 to 4 carbons, preferably methanol aqueous solution and ethanol aqueous solution, and water-saturated butyl alcohol.

The solvent used for preparing the solvent-soluble extract of *Coptidis Rhizoma* or *Pharbitidis Semen* may be one or more selected from the group consisting of 10 to 70% (v/v), preferably 20 to 60% (v/v), more preferably 25 to 55% (v/v) of linear or branched alcohol having 1 to 6 carbons, preferably propyl alcohol aqueous solution and isopropyl alcohol aqueous solution, and water-saturated butyl alcohol.

In another embodiment, the combined extract according to the present invention can be an extract of the mixture of *Coptidis Rhizoma* and *Pharbitidis Semen*. For example, the combined extract may be a crude extract obtained by mixing *Coptidis Rhizoma* and *Pharbitidis Semen*, and extracting the mixture with one or more solvents selected from the group consisting of water and linear or branched alcohol having 1 to 4 carbons, or a solvent-soluble extract obtained by adding one or more solvents selected from the group consisting of an aqueous solution of linear or branched alcohol having 1 to 6 carbons, preferably propyl alcohol aqueous solution and isopropyl alcohol aqueous solution, and water-saturated butyl alcohol, to the crude extract.

In a preferred embodiment, the solvent used for preparing the crude extract of *Coptidis Rhizoma* and *Pharbitis Semen* may be water, 10 to 70% (v/v), preferably 20 to 60% (v/v), more preferably about 25 to 55% (v/v) of methanol aqueous solution or ethanol aqueous solution, or water-saturated butyl alcohol. The solvent used for preparing the solvent-soluble extract may be one or more selected from the group consisting of 10 to 70% (v/v), preferably 20 to 60% (v/v), more preferably about 25 to 55% (v/v) of an aqueous solution of linear or branched alcohol 1 to 6 carbons, preferably propyl alcohol aqueous solution and isopropyl alcohol aqueous solution, and water-saturated butyl alcohol.

In another aspect, the present invention relates to a method of preparing a combined extract of *Coptidis Rhizoma* and *Pharbitidis Semen* having the activity of treating periodontal disease.

In one embodiment, the method of preparing the combined extract of *Coptidis Rhizoma* and *Pharbitidis Semen* may comprise the steps of:

extracting *Coptidis Rhizoma* with one or more solvents selected from the group consisting of water and linear or branched alcohol having 1 to 4 carbons, for example, water, 10 to 70% (v/v), preferably 20 to 60% (v/v), more preferably 25 to 55% (v/v) of methanol aqueous solution or ethanol aqueous solution, or water-saturated butyl alcohol, to obtain *Coptidis Rhizoma* extract;

extracting *Pharbitidis Semen*, preferably powdered *Pharbitidis Semen* with one or more solvents selected from the group consisting of water and linear or branched alcohol having 1 to 4 carbons, for example, water, 10 to 70% (v/v), preferably 20 to 60% (v/v), more preferably 25 to 55% (v/v) of methanol aqueous solution or ethanol aqueous solution, or water-saturated butyl alcohol, to obtain *Pharbitidis Semen* extract; and mixing the obtained *Coptidis Rhizoma* extract and *Pharbitidis Semen* extract at a ratio of 0.5:1 to 30:1 (the weight of *Coptidis Rhizoma* extract:the weight of *Pharbitidis Semen* extract), preferably 1:1 to 25:1, more preferably 2.5:1 to 20:1, most preferably 7.5:1 to 15:1, based on the dry matter content.

The step of preparing *Coptidis Rhizoma* extract and the step of preparing *Pharbitidis Semen* extract may further comprise the step of adding one or more solvents selected from the group consisting of linear or branched alcohol having 1 to 6 carbons, preferably water-saturated butyl alcohol, propyl alcohol and isopropyl alcohol to the obtained extract, to obtain a solvent-soluble extract.

The step of preparing *Coptidis Rhizoma* extract will be explained in detail: *Coptidis Rhizoma* is chopped into small pieces, and then, one or more solvents selected from the group consisting of water and linear or branched alcohol having 1 to 4 carbons, for example, water, 10 to 70% (v/v), preferably 20 to 60% (v/v), more preferably 25 to 55% of methanol aqueous solution or ethanol aqueous solution, or water-saturated butyl alcohol, is added thereto in an amount of about 5 to 20 times by volume, preferably 7 to 15 times by volume of the raw material for reflux-extraction. The extraction temperature is, although not specifically limited, preferably 40 to 110° C., preferably 55 to 90° C.

Preferably, the obtained extract is filtered to collect filtrate, and one or more solvents selected from the group consisting of water and linear or branched alcohol having 1 to 4 carbons, for example, water, 10 to 70% (v/v), preferably 20 to 60% (v/v), more preferably 25 to 55% of methanol aqueous solution or ethanol aqueous solution, or water-saturated butyl alcohol, is added to the reside in an amount of about 5 to 15 times by volume, preferably 8 to 12 times by volume for reflux-extraction. The extraction temperature is, although not specifically limited, preferably 40 to 110° C., preferably 55 to 90° C. After the extraction, the extract is filtered, combined with the filtrate obtained previously and concentrated under the vacuum to obtain *Coptidis Rhizoma* extract. Combination of the obtained extract with previously obtained filtrate can increase extraction efficiency, but there is no limitation in the number of extractions for the extract of the present invention.

If the amount of the solvent used for preparing *Coptidis Rhizoma* extract is too small, stirring is difficult and solubility of the extract decreases to lower extraction efficiency. If the amount of the solvent used for preparing *Coptidis Rhizoma* extract is too much, the amount of lower alcohol for next purification step becomes increased to cause economical problems and problems in handling. Thus, it is preferable to adjust the amount of the solvent within the above described range.

According to one preferred embodiment of the present invention, re-extraction may be made after primary extraction, which is to prevent decrease in extraction efficiency by performing primary extraction only, because in case herb extract is produced in large quantity, even if effective filtration is made, the water content is high, thereby generating losses thereof, and thus, the extraction efficiency becomes decreased when only primary extraction is performed. Therefore, according to one preferred embodiment of the present invention, re-extraction may be made after primary extraction. In addition, as result of examining extraction efficiency in each step, it has been found that about 80 to 90% of total extract amount is extracted by secondary extraction, and thus, it may be suggested that two-step extractions allows significant economical efficacy compared to multistep extractions more than third extraction.)

In order to control the content of the remaining lower alcohol in the obtained concentrate so as to make it suitable for use as pharmaceutical ingredient, the concentrate may be subjected to azeotropic concentration with about 10 to 30 times, preferably 15 to 25 times, more preferably about 20 times by weight of water, based on the total amount of the concentrate, for 1 to 5 times, preferably 2 to 3 times, and equivalent amount of water is added thereto to homogeneously suspend it, and then, the suspension is lyophilized to prepare *Coptidis Rhizoma* extract in powder form.

The step of preparing *Pharbitidis Semen* extract will be explained in detail: *Pharbitidis Semen* is grinded and then, one or more solvents selected from the group consisting of water and linear or branched alcohol having 1 to 4 carbons, for example, water, 10 to 70% (v/v), preferably 20 to 60% (v/v), more preferably 25 to 55% of methanol aqueous solution or ethanol aqueous solution, or water-saturated butyl alcohol, is added thereto in an amount of about 3 to 20 times by volume, preferably 5 to 15 times by volume of the raw material to extract for 1 to 10 hours, preferably 2 to 5 hours. The extraction temperature is, although not specifically limited, preferably 40 to 110° C., preferably 55 to 90° C. Preferably, the obtained extract is filtered to collect filtrate, and one or more solvents selected from the group consisting of water and linear or branched alcohol having 1 to 4 carbons, for example, water, 10 to 70% (v/v), preferably 20 to 60% (v/v), more preferably 25 to 55% of methanol aqueous solution or ethanol aqueous solution, or water-saturated butyl alcohol, is added to the reside in an amount of about 1 to 10 times by volume, preferably 4 to 7 times by volume, and temperature is elevated to re-extract for 1 to 10 hours, preferably 2 to 5 hours, and then, the extract is filtered and concentrated under the vacuum to obtain *Pharbitidis Semen* extract. Combination of the obtained extract with previously obtained filtrate can increase extraction efficiency, but there is no limitation in the number of extractions for the extract of the present invention.

The double extractions and combination of the filtrates obtained after each extraction may increase extraction efficiency, but the number of extraction is not limited thereto.

If the amount of the solvent used for preparing *Pharbitidis Semen* extract is too small, stirring is difficult and solubility of the extract decreases to lower extraction efficiency. If the amount of the solvent used for preparing *Pharbitidis Semen* extract is too much, the amount of lower alcohol for next purification step becomes increased to cause economical problems and problems in handling. Thus, it is preferable to adjust the amount of the solvent within the above described range.

According to one preferred embodiment of the present invention, re-extraction may be made after primary extraction, which is to prevent decrease in extraction efficiency by performing primary extraction only, because in case herb extract is produced in large quantity, even if effective filtration is made, the water content is high, thereby generating losses thereof, and thus, the extraction efficiency becomes decreased when only primary extraction is performed. Therefore, according to one preferred embodiment of the present invention, re-extraction may be made after primary extraction. In addition, as result of examining extraction efficiency in each step, it has been found that about 80 to 90% of total extract amount is extracted by secondary extraction, and thus, it may be suggested that two-step extractions allows significant economical efficacy compared to multistep extractions more than third extraction.

The step of solvent-soluble extraction by means of solvent partition 1 to 10 times, preferably 2 to 4 times using the same amount of lower alcohol as the above filtrate can be used additionally to purify unnecessary impurities such as proteins, polysaccharides, fatty acids, and the like after filtering and concentrating the *Coptidis Rhizoma* extract and/or *Pharbitidis Semen* extract obtained from primary and secondary extraction with methanol aqueous solution, ethanol aqueous solution, or water-saturated butyl alcohol. The above lower alcohols include linear or branched alcohols having 1 to 6 carbons, preferably can be selected from the group of one or more alcohols consisting of one or more butyl alcohol, propyl alcohol, isopropyl alcohol and water-saturated butyl alcohol. If the amount of the lower alcohol used therefore is small compared to filtrate, fine particles form of unnecessary ingredients such as fatty acid, thereby making solvent partition unsmooth and decreasing extraction amount of active ingredients. Therefore, it may be preferable to adjust the amount of the lower alcohol within the above described range.

The lower alcohol fraction obtained after solvent partition is concentrated under the vacuum at 50 to 60π C. to remove remaining solvent in the sample.

In order to control the content of the remaining lower alcohol in the obtained concentrate so as to make it suitable for use as pharmaceutical ingredient, the concentrate may be subjected to azeotropic concentration with about 10 to 30 times, preferably 15 to 25 times, more preferably about 20 times by weight of water, based on the total amount of the concentrate, for 1 to 5 times, preferably 2 to 3 times, and equivalent amount of water is added thereto to homogeneously suspend it, and then, the suspension is lyophilized to prepare *Pharbitidis Semen* extract in semi-solid or dry state.

The preparation process of the combined composition of the two extracts as prepared above is as follows.

The *Coptidis Rhizoma* extract and *Pharbitidis Semen* extract obtained above are mixed, at a dry matter weight ratio of 0.5:1 to 30:1 (the weight of *Coptidis Rhizoma* extract:the weight of *Pharbitidis Semen* extract), preferably 1:1 to 25:1, more preferably 2.5:1 to 20:1 m and most preferably 7.5:1 to 15:1.

In order to mix each extract in the above combined extract homogeneously, about 2 to 3 times by weight of water is added to the combined extract, and then it is concentrated under vacuum at 50 to 60° C., equivalent amount of water is added again to the concentrate to homogeneously suspend it, and then the suspension is lyophilized to prepare the composition in powder form.

According to another embodiment, the above preparation method may comprise the steps of:

mixing *Coptidis Rhizoma* and *Pharbitidis Semen*, preferably the powdered *Pharbitidis Semen* thereof at a weight ratio of 0.2:1 and 25:1 (the weight of *Coptidis Rhizoma*: the weight of *Pharbitidis Semen*), preferably 0.5:1 to 20:1, more preferably 1.5:1 to 15:1 to prepare a mixture of *Coptidis Rhizoma* and *Pharbitidis Semen*; and extracting the mixture of *Coptidis Rhizoma* and *Pharbitidis Semen* with one or more solvents selected from the group consisting of water and linear or branched alcohol having 1 to 4 carbons, for example, water, 10 to 70% (v/v), preferably 20 to 60% (v/v), more preferably about 25 to 55% (v/v) of methanol aqueous solution or ethanol aqueous solution, or water-saturated butyl alcohol.

The above method may further comprise the step of adding one or more solvents selected from the group consisting of linear or branched alcohol having 1 to 6 carbons, preferably propyl alcohol, isopropyl alcohol and water-saturated butyl alcohol, to obtain solvent-soluble extract, after the step of obtaining extract of the mixture of *Coptidis Rhizoma* and *Pharbitidis Semen*.

The details of the steps of preparing the above crude extract and the solvent-soluble extract are as described in the preparation of each herb extract as above.

As the extraction method used in the present invention, any conventionally used method may be used. For examples, the extraction may be performed through extraction at cold temperature, hot water extraction, ultrasonic extraction, or reflux extraction, but not limited thereto.

The present invention provides a composition for the prevention and treatment of periodontal disease comprising the extract of *Coptidis Rhizoma* or combined extract of *Coptidis Rhizoma* and *Pharbitidis Semen* as active ingredients.

In addition, the combined extract of *Coptidis Rhizoma* and *Pharbitidis Semen* as well as the extract of *Coptidis Rhizoma* alone may be used for the prevention, treatment or relief of the symptoms of periodontal disease, because the combined extract has higher activities for anti-inflammation and osteoblast differentiation. Therefore the present invention provides a composition for the prevention and treatment of periodontal disease comprising the extract of *Coptidis Rhizoma* or combined extract of *Coptidis Rhizoma* and *Pharbitidis Semen* as active ingredients.

The above periodontal disease is one or more selected from a group consisting of stomatitis, gingivitis, periodontitis, alveolar bone damage, alveolar osteoporosis, alveolar osteomalacia, alveolar bone loss, and alveolar osteochondrodysplasia.

The content of the extract as active ingredients in the composition of the present invention may vary depending on the type and objectives of the use, condition of the patient and the seriousness of the disease, and is in the dry matter content range of 0.001 to 99.9 weight %, preferably 0.1 to 50 weight %, but is not limited thereto.

The composition of the present invention may be administered to mammals including human in various routes. It can be administered using commonly used method, for examples, it can be administered orally, intrarectally, or by intravenous, intramuscular, subcutaneous, intrauterine or intracerebroventricular injection, and preferably orally. The composition of the present invention may be formulated into an oral dosage form such as powder, granule, tablet, capsule, suspension, emulsion, syrup, aerosol, etc., or a non-oral dosage form such as transdermal agent, suppository and sterile injection solution, etc.

The composition of the present invention may further comprise pharmaceutically suitable and physiologically acceptable adjuvant such as carrier, excipients and diluents including lactose, dextrose, sucrose, sorbitol, mannitol, xylitol, erithrytol, maltitol, starch, acacia rubber, alginate, gelatin, calcium phosphate, calcium silicate, cellulose, methyl cellulose, amorphous cellulose, polyvinylpyrrolidone, water, methylhydroxybenzoate, propylhydroxybenzoate, talc, magnesium stearate and mineral oil. In case of formulation, commonly used diluents or excipients such as fillers, extender, binder, humectant, disintegrant and surfactant can be used. Solid formulations for oral administration include tablets, pills, powder, granules and capsules, and can be prepared by mixing the above extract with one or more excipients such as starch, calcium carbonate, sucrose, lactose or gelatin. Also lubricants such as magnesium stearate and talc can be used instead of simple excipients.

Liquid formulations for oral administrations include suspension, liquid and solution, emulsion, syrup, and frequently used water, liquid paraffin and other excipients such as humectant, sweetener, aromatics and preservatives can also be used. In the formulations for non-oral administration, sterilized aqueous solution, non-aqueous solvent, suspension, emulsion, freeze-dried formulation, rectal suppository and transcutaneous formulation are included. Propylene glycol, polyethylene glycol, vegetable oil, such as olive oil, and injectable esters, such as ethyloleate, can be used as non-aqueous solvent or suspension. The base for suppository includes witepsol, macrogol, tween 61, cacao oil, laurin oil, glycerol and gelatin.

The pharmaceutical composition of the present invention may be administered to human as a single formulation, but can also be administered by using general protocols or by mixing with pharmaceutical carriers selected in consideration of the standard pharmaceutical practice. For examples, the pharmaceutical composition of the present invention can be dose via oral, buccal or sublingual administration in the form of tablets containing starch or lactose, capsules alone or with excipients, or elixir or suspension with chemicals for taste masking or coloration. Such liquid formulations can be formulated with pharmaceutically acceptable additives such as suspensions (for instance methyl cellulose, semisynthetic glyceride such as witepsol, mixture of apricot kernel oil and PEG-6 esters, glyceride mixtures such as PEG-8 and caprylic/capric glyceride).

The administration dose of the pharmaceutical composition of the present invention may vary depending on the age, weight, health status and seriousness of the disease of the patient and administration type, and can be once or number of times a day at fixed time interval depending on the judgment of physician or pharmacist.

For instance, daily dose of the effective ingredient can be 0.1 to 500 mg/kg, and preferably 0.5 to 300 mg/kg. The above dose is only an average value, and the dose can be higher or lower depending on the personal differences. It is preferable to have the above dose range since meaningful effect cannot be obtained when the daily dose of the pharmaceutical composition of the present invention is lower than the above dose and it is not only uneconomical, but also can cause undesirable side-effects if the dose is higher.

In another aspect, the present invention provides a health functional food for the improvement and/or prevention of periodontal disease comprising the extract of *Coptidis Rhizoma* or a combined extract of *Coptidis Rhizoma* and *Pharbitidis Semen*. The health functional food may be various foods, beverage, or food additives, etc.

The content of the extract as an active ingredient contained in the health functional food can be appropriately varied depending on the form of food, desired use, etc., without specific limitations. For example, it can be added in an amount of 0.01 to 15 wt % of the total food, and for health beverage composition, it can be added in an amount of 0.02 to 10 g, preferably 0.3 to 1 g, based on 100 ml of the composition.

The liquid composition in the health beverage composition does not have specific limitations except to have the above extract at specific ratios as an essential ingredient, and includes various cordials or natural carbohydrates. The above natural carbohydrates include monosaccharides such as dextrose, fructose, disaccharides such as maltose and sucrose, polysaccharides, conventional sugars, such as dextrin and cyclodextrin and sugar alcohols such as xylitol, sorbitol and erythritol.

Cordials besides the described above, natural cordials (thaumatin, stevia extracts (for example rebaudioside A, glycyrrhizin and etc.)) and synthetic cordials (saccharin, aspartame and etc.) can be used effectively. The above natural carbohydrates can be added in an amount of 1 to 20 g, preferably 5 to 12 g, based on 100 ml of the composition.

The composition of the present invention can also include various nutrients, vitamins, minerals (electrolytes), flavoring agents such as synthetic and natural flavoring agents, coloring agents, thickening agent (cheese or chocolate), pectic acid and its salt, alginic acid and its salt, organic acid, protective colloid viscosity agents, pH controlling agent, stabilizer, antiseptic agent. Glycerin, alcohol and carbonation agent used in the carbonated drinks. The composition of the present invention can also include natural fruit juice and fruit juice beverage and pulp to prepare vegetable drinks. The above ingredients can be used independently or in combination. The ratio of these additives is not important, but is selected in general to be 0 to 20 parts by weight parts, based on 100 parts by weight.

Yet in another aspect, the present invention provides oral products containing the above *Coptidis Rhizoma* extract or a combined extract of *Coptidis Rhizoma* and *Pharbitidis Semen*. The above oral products have an effect on the preventing and improving periodontal disease. The above oral products can include toothpaste, mouth wash, oral spray, chewing gum, ointment and patches.

The above oral products can also include additives selected from a group of abrasives, humectant, binder, foaming agents, sweetener, preservatives, efficacy agent, flavoring agent, acidity controlling agent, and whitening agent.

For example, the above abrasives can include one or more selected from a group of dicalcium phosphate, precipitated silica, calcium carbonate, aqueous alumina, kaolin, and sodium bicarbonate, and the content of the abrasives can be in the range from 20 to 60 weight % (of total weight, the same hereinafter), but is not limited thereto. The above humectant can include one or more selected from a group of glycerin, sorbitol, noncrystallizing sorbitol solution, propylene glycol, polyethylene glycol, and xylitol, and the content of the humectant can be in the range from 20 to 60 weight %, but is not limited thereto. The above binder can include one or more selected from a group of carrageenan, xanthan gum, sodium carboxy methyl cellulose, carboxyvinyl polymer, sodium alginate, and laponite, and the content of the abrasives can be in the range from 0.1 to 3.0 weight %, preferably 0.5 to 2.0 weight %, but is not limited thereto. The above foaming agent can include one or more selected from a group of anionic surfactants such as sodium lauryl sulfate and sodium lauroyl sarcosinate, condensed polymers such as sorbitan fatty acid ester, polyoxyethylene hydrogenated castor oil, and polyoxyethylene, polyoxyepropylene, and the content of the abrasives can be in the range from 0.5 to 5.0 weight %, preferably 0.5 to 3.5 weight %, but is not limited thereto. The above sweeteners can include one or more than two selected from a group of sodium saccharinate, aspartame and glycyrrhizinic acid, and the content of the humectant can be in the range from 0.05 to 0.5 weight %, but is not limited thereto. The above preservatives can include one or more than two selected from a group of p-oxybenzoic acid ester, and sodium benzoate. The above efficacy agent can include sodium fluoride, acidulated phosphate fluoride, tin fluoride, amine fluoride, chlorhexidine, tranexamic acid, allantoins, caproic acid, polyphosphates, enzymes and herbal extracts. The flavoring agent can include peppermint oil, spearmint oil, menthol, and carvone mixed in appropriate ratios. The above acidity controlling agent can include phosphoric acid, sodium phosphate, citric acid, sodium citrate, succinic acid, sodium succinate, tartaric acid, and sodium tartarate, and the preferable acidity is 5 to 8. The above whitening agent can be titanic oxide and can be in the range from 0.1 to 2 weight %, but is not limited thereto.

The herbal extract according to the present invention is expected to have less side-effects when administered to human considering the general characteristics of natural extracts, and also the standardized composition did not show any toxicity in animals.

The extract of *Coptidis Rhizoma* alone or the combined extract of *Coptidis Rhizoma* and *Pharbitidis Semen* according to the present invention has characteristics of increasing anti-inflammatory activity, osteoblast differentiation and alveolar bone regeneration, of decreasing the alveolar bone destruction.

EXAMPLES

The present invention will be explained in detail with reference to the following examples and experiments.

However, the following examples and experiments are only to illustrate the present invention, and the scope of the present invention is not limited thereto.

Example 1

Preparation of Herbal Extract 1.1. Preparation of the Extract of *Coptidis Rhizoma*

*Coptidis Rhizoma* (root region) was washed with water to remove impurities and dried completely. Prepared 250 g of *Coptidis Rhizoma* was reflux-extracted with 2.0 L of 50% (v/v) ethanol aqueous solution at 80° C. twice each for 3 hours, and then, the extract was filtered and concentrated under the vacuum to obtain 57.5 g of crude extract. In this crude extract, 0.3 L of water was added to suspend it, and 0.6 L of water-saturated butyl alcohol was added thereto, to separate a layer twice, and then, only water-saturated butyl alcohol fraction was collected and concentrated under the vacuum until dried. When most of butyl alcohol and water was evaporated, 0.2 L of water was added to azeotropically concentrate it, which was repeated twice. And, finally, distilled water of equal amount was added to suspend the concentrate, and then, the suspension was lyophilized to obtain 31.8 g of *Coptidis Rhizoma* extract in powder form.

1.2. Preparation of the Extract of *Pharbitidis Semen*

*Pharbitidis Semen* was washed with water to remove impurities, dried completely and ground to obtain powder. Prepared 250 g of *Pharbitidis Semen* was reflux-extracted with 2.0 L of 50% (v/v) ethanol aqueous solution at 80° C. twice each for 3 hours, and then, the extract was filtered and concentrated under the vacuum to obtain 33.3 g of crude extract. In this crude extract, 0.3 L of water was added to suspend it, and 0.6 L of water-saturated butyl alcohol was added thereto, to separate a layer twice, and then, only water-saturated butyl alcohol fraction was collected and concentrated under the vacuum until dried. When most of butyl alcohol and water was evaporated, 0.2 L of water was added to azeotropically concentrate it, which was repeated twice. And, finally, distilled water of equal amount was added to suspend the concentrate, and then, the suspension was lyophilized to obtain 6.9 g of *Pharbitidis Semen* extract in powder form.

Example 2

Preparation of the Combined Extract of *Coptidis Rhizoma* Extract and *Pharbitidis Semen* Extract Preparation Example 1

Combined Extract (1:1)

The *Coptidis Rhizoma* extract prepared in the above Example 1.1 and the *Pharbitidis Semen* extract prepared in the above Example 1.2 were mixed at a weight ratio of 1:1 (the weight of *Coptidis Rhizoma* extract:the weight of *Pharbitidis Semen*). In order to mix them homogeneously, about 2 to 3 times by weight of water was added to the combined extract, and then it was concentrated under the vacuum at a temperature of 50 to 60° C. And, an equivalent amount of water was added again to the obtained concentrate to suspend it homogeneously, and the suspension was lyophilized to prepare a combined extract in powder form.

Preparation Example 2

Combined Extract (2.5:1)

A combined extract was prepared by the same method as the above Preparation Example 1, except that the ratio of the *Coptidis Rhizoma* extract prepared in the above Example 1.1 and the *Pharbitidis Semen* extract prepared in the above Example 1.2 was 2.5:1 (the weight of *Coptidis Rhizoma* extract:the weight of *Pharbitidis Semen*)

Preparation Example 3

Combined Extract (5:1)

A combined extract was prepared by the same method as the above Preparation Example 1, except that the ratio of the *Coptidis Rhizoma* extract prepared in the above Example 1.1 and the *Pharbitidis Semen* extract prepared in the above Example 1.2 was 5:1 (the weight of *Coptidis Rhizoma* extract:the weight of *Pharbitidis Semen*)

Preparation Example 4

Combined Extract (7.5:1)

A combined extract was prepared by the same method as the above Preparation Example 1, except that the ratio of the *Coptidis Rhizoma* extract prepared in the above Example 1.1 and the *Pharbitidis Semen* extract prepared in the above Example 1.2 was 7.5:1 (the weight of *Coptidis Rhizoma* extract:the weight of *Pharbitidis Semen*)

Preparation Example 5

Combined Extract (10:1)

A combined extract was prepared by the same method as the above Preparation Example 1, except that the ratio of the *Coptidis Rhizoma* extract prepared in the above Example 1.1 and the *Pharbitidis Semen* extract prepared in the above Example 1.2 was 10:1 (the weight of *Coptidis Rhizoma* extract:the weight of *Pharbitidis Semen*)

Preparation Example 6

Combined Extract (12.5:1)

A combined extract was prepared by the same method as the above Preparation Example 1, except that the ratio of the *Coptidis Rhizoma* extract prepared in the above Example 1.1 and the *Pharbitidis Semen* extract prepared in the above Example 1.2 was 12.5:1 (the weight of *Coptidis Rhizoma* extract:the weight of *Pharbitidis Semen*)

Preparation Example 7

Combined Extract (15:1)

A combined extract was prepared by the same method as the above Preparation Example 1, except that the ratio of the *Coptidis Rhizoma* extract prepared in the above Example 1.1 and the *Pharbitidis Semen* extract prepared in the above Example 1.2 was 15:1 (the weight of *Coptidis Rhizoma* extract:the weight of *Pharbitidis Semen*)

Preparation Example 8

Combined Extract (17.5:1)

A combined extract was prepared by the same method as the above Preparation Example 1, except that the ratio of the *Coptidis Rhizoma* extract prepared in the above Example 1.1 and the *Pharbitidis Semen* extract prepared in the above Example 1.2 was 17.5:1 (the weight of *Coptidis Rhizoma* extract:the weight of *Pharbitidis Semen*)

Preparation Example 9

Combined Extract (20:1)

A combined extract was prepared by the same method as the above Preparation Example 1, except that the ratio of the *Coptidis Rhizoma* extract prepared in the above Example 1.1 and the *Pharbitidis Semen* extract prepared in the above Example 1.2 was 20:1 (the weight of *Coptidis Rhizoma* extract:the weight of *Pharbitidis Semen*)

Preparation Example 10

Combined Extract (22.5:1)

A combined extract was prepared by the same method as the above Preparation Example 1, except that the ratio of the *Coptidis Rhizoma* extract prepared in the above Example 1.1 and the *Pharbitidis Semen* extract prepared in the above Example 1.2 was 22.5:1 (the weight of *Coptidis Rhizoma* extract:the weight of *Pharbitidis Semen*)

Preparation Example 11

Combined Extract (25:1)

A combined extract was prepared by the same method as the above Preparation Example 1, except that the ratio of the *Coptidis Rhizoma* extract prepared in the above Example 1.1 and the *Pharbitidis Semen* extract prepared in the above Example 1.2 was 25:1 (the weight of *Coptidis Rhizoma* extract:the weight of *Pharbitidis Semen*)

Example 3

Measurement of Pharmacological Activity

Experimental Example 1

Osteoblast Proliferation Activity

Figure 1:
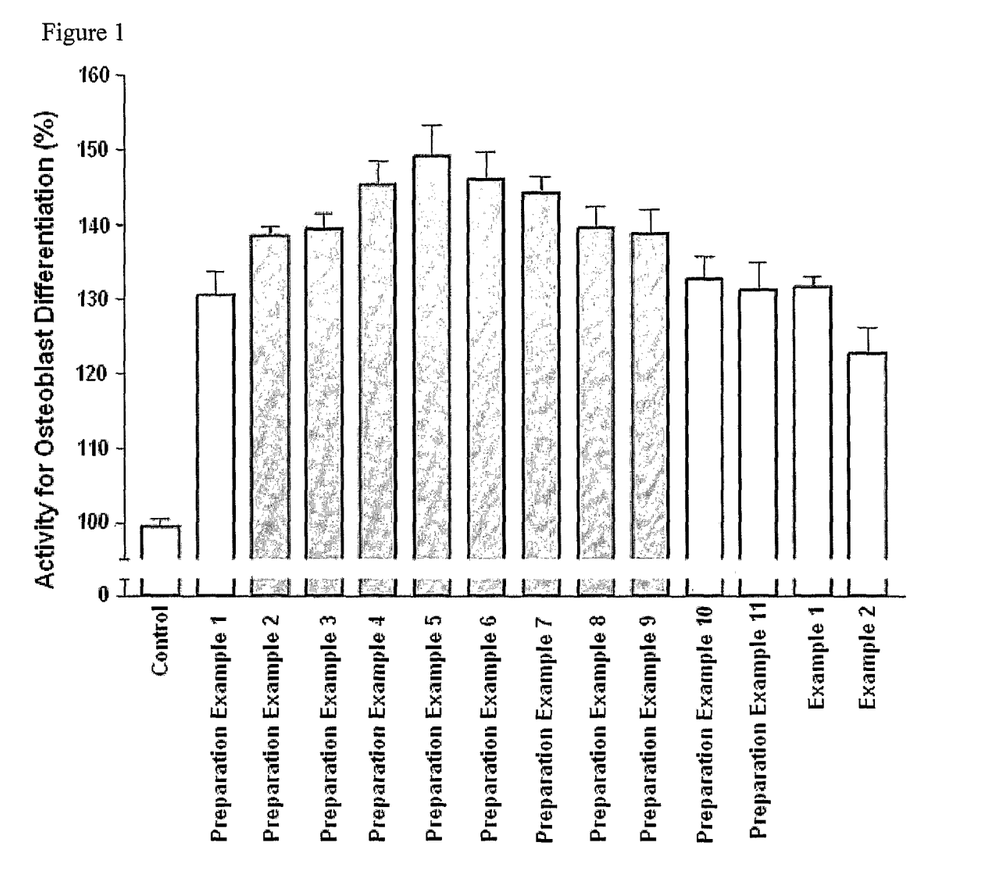
FIG. 1 is a result showing the activity of increasing osteoblast differentiation for the extracts of the Preparation Examples 1 to 11 and Examples 1.1 and 1.2.

In order to evaluate the osteoblast proliferation activity for the combined extracts prepared in the above Preparation Examples 1 to 11 and the single extract prepared in Examples 1.1 and 1.2, the activity was tested with MG-63 cell line (human osteoblast, Korean Cell Line Bank, KCLB No. 21427) by using BrdU kit (cell proliferation ELISA, Roche) following the methods by Lim et al. (Lim S et al., *Korean J. Food Sci. Technol*, 39, 694-700. 2007), and the result is shown in FIG. 1.

Experimental Procedures

MG-63 cells cultured in DMEM (Dulbecco's Modified Eagle's medium, Cambrex, USA) supplemented with 10% fetal bovine serum was placed in 96 well plate at 1×10$^4$ cell/mL concentration and stabilized for 24 hours in CO$_2$ incubator (5% carbon dioxide, 95% relative humidity, 37° C.) and the above combined extract or singe extract at a final concentration of 3 ug/mL was added. After BrdU was treated to each well and cultivated for 12-16 hours and cells fixed, anti BrdU solution (perioxidase-conjugated anti-BradU antibody, Roche) and substrate (TMB (3,3',5,5'-Tetramethylbenzidine) substrate solution, Roche) 200 uL was added for color reaction. The reaction was terminated with 1M H$_2$SO$_4$ 25 uL and the activity of osteoblast proliferation was evaluated by measuring absorbance at 450 nm using spectrophotometer.

Experimental Results

The osteoblast proliferation activity for the *Coptidis Rhizoma* extract prepared in Examples 1.1 and the *Pharbitidis Semen* extract prepared in 1.2 and the combined extracts prepared in the above Examples 1 to 11 was evaluated and the result is shown in FIG. 1. As shown in FIG. 1, the *Coptidis Rhizoma* extract prepared in Examples 1.1 and the *Pharbitidis Semen* extract prepared in 1.2 and the combined extracts prepared in the above Preparation Examples 1 to 11 had osteoblast proliferation activity. Furthermore, the extracts in Preparation Examples 2 to 9 showed higher osteoblast proliferation activity confirming pharmacological synergistic effect for the combined compositions according to the present invention. When the *Coptidis Rhizoma* extract and the *Pharbitidis Semen* extract was mixed to 7.5:1 and 15:1 in Preparation Examples 4 to 7, the osteoblast proliferation activity was especially higher. When the *Coptidis Rhizoma* extract and the *Pharbitidis Semen* extract was mixed to 10:1 in Preparation Example 5, the osteoblast proliferation activity was highest.

Experimental Example 2

In Vitro Anti-Inflammatory Activity

In order to evaluate the in vitro anti-inflammatory activity for the combined extracts prepared in the above Preparation Examples 1 to 11 and the single extract prepared in Examples 1.1 and 1.2, the activity was tested by measuring the formation of stable NO oxide (NO$_3^-$) with LPS-activated mouse leukemic monocyte macrophage cell line, RAW 264.7 cell line (RAW 264.7 cells hereafter, American Type Cell Culture, ATCC #TIB-71) by modifying the methods of Sherman et al. (Sherman et al., *Biochem. Biophys. Res. Commun.* 191, 1301-1308, 1993), and the result is shown in Table 1.

Experimental Procedures

RAW 264.7 cells cultured in DMEM (Dulbecco's Modified Eagle's medium, Cambrex, USA) supplemented with 10% fetal bovine serum was placed in 48 well plate at 2.5×10$^5$ cell/mL concentration, activation was induced by adding LPS (10 ng/mL), the above combined extract and single extract was added at the final concentration of 3 ug/mL and stabilized for 24 hours in CO2 incubator (5% carbon dioxide, 95% relative humidity, 37° C.). In 50 uL of each supernatant, 50 uL of Griess reagent (37.5 mM ulphanilic acid, 12.5 mM N-1-naphthyl-etylenediamine dihydride, 6.5 mM HCl) was added and reacted for 10 min at room temperature. The in vitro anti-inflammatory activity was evaluated by determining the concentration of NO$_3^-$ by measuring the absorbance at 540 nm using spectrophotometer.

Experimental Results

The in vitro anti-inflammatory activity for *Coptidis Rhizoma* extract prepared in Examples 1.1 and for *Pharbitidis Semen* extract prepared in Examples 1.2 and the combined extracts prepared in the above Preparation Examples 1 to 11 was evaluated and shown in the below Table 1.

TABLE 1

| | Dosage (μg/ml) | Inhibition of NO synthesis (%) |
| --- | --- | --- |
| Preparation Example 1 | 3 | 63 |
| Preparation Example 2 | 3 | 71 |
| Preparation Example 3 | 3 | 75 |
| Preparation Example 4 | 3 | 79 |
| Preparation Example 5 | 3 | 85 |
| Preparation Example 6 | 3 | 85 |
| Preparation Example 7 | 3 | 78 |
| Preparation Example 8 | 3 | 74 |
| Preparation Example 9 | 3 | 72 |
| Preparation Example 10 | 3 | 67 |
| Preparation Example 11 | 3 | 63 |
| Example 1.1 | 3 | 63 |
| Example 1.2 | 3 | 67 |

As shown in Table 1, the *Coptidis Rhizoma* extract prepared in Examples 1.1 and the *Pharbitidis Semen* extract prepared in 1.2 and the combined extracts prepared in the above Preparation Examples 1 to 11 had anti-inflammatory activity suppressing NO production. Furthermore, the extracts in Preparation Examples 2 to 9 showed higher anti-inflammatory activity confirming pharmacological synergistic effect for the combined compositions according to the present invention. When the *Coptidis Rhizoma* extract and

*Pharbitidis Semen* extract was mixed to 7.5:1 and 15:1 in Preparation Examples 4 to 7, the anti-inflammatory activity was especially higher. When the *Coptidis Rhizoma* extract and *Pharbitidis Semen* extract was mixed to 10:1 to 12.5:1 in Preparation Examples 5 and 6, the anti-inflammatory activity was highest.

Experimental Example 3

In Vivo Anti-Inflammatory Activity

In order to evaluate in vivo anti-inflammatory activity of the combined extract prepared in Preparation Examples 4 to 7 showing improved osteoblast proliferation and anti-inflammatory activity in the above Experimental Examples 1 and 2 and single extract in Examples 1.1 and 1.2, Hee et. al.'s method was used for the evaluation (*Kor. J. Pharmacogn.* 25(4), 363~367, 1994, *Arch. Pharm. Res.* 16(1), 18~24, 1993.), and the result is shown in Table 2. In Table 2, 20 mg/kg was administered for positive control (Indomethacin, Sigma) and 200 mg/kg was administered for the test groups orally. Dose dependent anti-inflammatory activity was evaluated for the Example 5 with the highest activity, and the result is shown in Table 3.

Experimental Procedures

The thickness of ear was measured by using a thickness gauge (model H, Peacock, Japan) for male ICR mice (6 weeks, Samtaco Biokorea) before treating with the formulation. The control and test drug was administered orally, and the inflammation was induced 1 hour after the administration by smearing 10 uL of inflammation inducing material (2.5% croton oil, sigma) dissolved in acetone on the inner and outer ear after immobilizing the mice. In 5 hours, the mice were sacrificed by cervical dislocation and the thickness of the right ear was measured.

Experimental Results

Anti-inflammatory activity was measured for indomethacin used as positive control and the *Coptidis Rhizoma* extract prepared in Examples 1.1 and the *Pharbitidis Semen* extract prepared in 1.2 and the combined extracts prepared in the above Preparation Examples 4 to 7 is shown in Table 2, and the dose dependent Anti-inflammatory activity for the combined extract in Preparation Example 5 is shown in Table 3.

TABLE 2

|  | Dosage (mg/kg) | Anti-inflammatory activity (%) |
| --- | --- | --- |
| Preparation Example 4 | 200 | 62 |
| Preparation Example 5 | 200 | 70 |
| Preparation Example 6 | 200 | 65 |
| Preparation Example 7 | 200 | 60 |
| Example 1.1 | 200 | 48 |
| Example 1.2 | 200 | 50 |
| Positive control   Indomethacin | 20 | 50 |

TABLE 3

|  | Dosage (mg/kg) | Anti-inflammatory activity (%) |
| --- | --- | --- |
| Preparation Example 5 | 50 | 42 |
|  | 100 | 53 |
|  | 150 | 64 |
|  | 200 | 70 |
| Positive control   Indomethacin | 20 | 50 |

As shown in Table 2, the *Coptidis Rhizoma* extract prepared in Examples 1.1 and the *Pharbitidis Semen* extract prepared in 1.2 and the combined extracts prepared in the above Preparation Examples 4 to 7 had anti-inflammatory activity. Furthermore, the extracts in Preparation Examples 4 to 7 showed higher anti-inflammatory activity confirming pharmacological synergistic effect for the combined compositions according to the present invention. Also Table 3 shows dose dependency for the combined extract in Preparation Example 5, and the combined extract at 50 mg/kg dose showed similar effect to the positive control, and higher at 100 mg/kg than the positive control.

Experimental Example 4

Efficacy for Periodontal Disease in Animal Model

Figure 2:
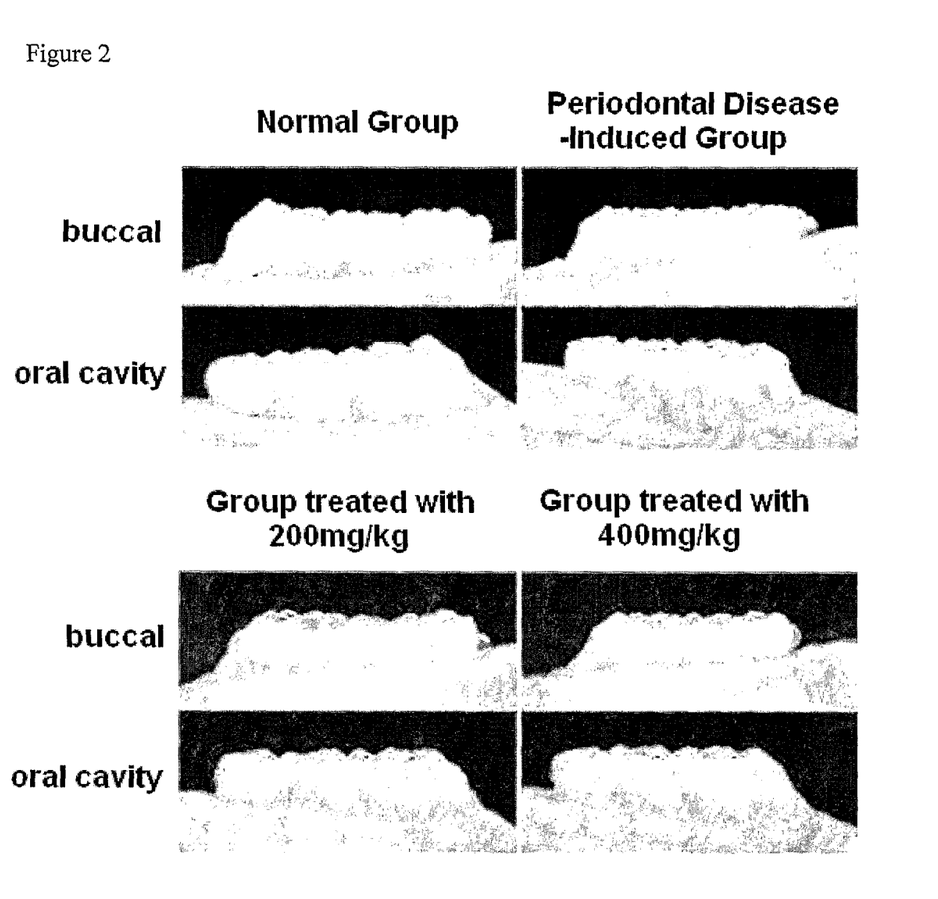
FIG. 2 is a CT image showing the activity of decreasing the absorption of alveolar bone (presented by alveolar bone destruction) in an animal model with periodontal disease for the combined extract of the Preparation Example 5.
Figure 3:
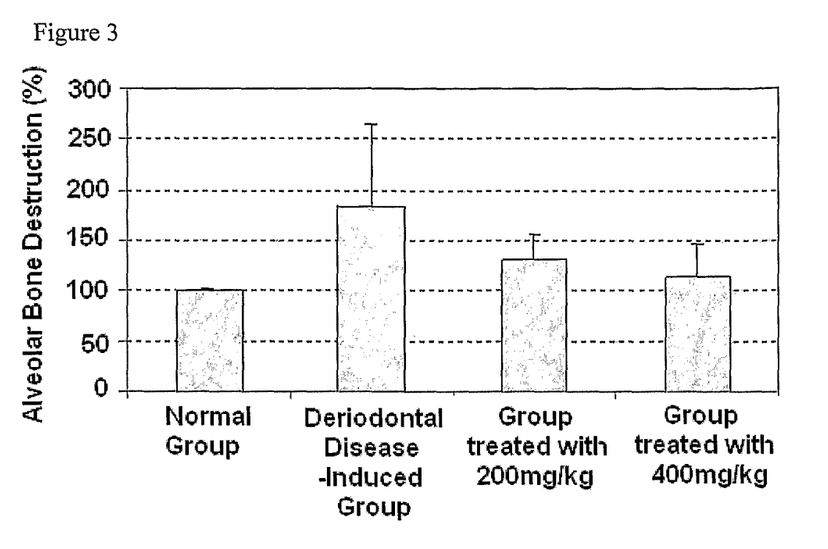
FIG. 3 is a graph showing the activity of decreasing the absorption of alveolar bone in an animal model with periodontal disease for the combined extract of the Preparation Example 5. (Showing the distance between Alveolar bone crest (AC) to Cemento-Enamel Junction (CEJ)).

In order to measure the efficacy in the periodontal disease animal model for the combined extract in Preparation Example 5 showing a high osteoblast proliferation activity and in vivo anti-inflammation activity, evaluation was made by using the method of Cai et al. (Cai et al., J. Periodont. Res. 43, 14-21, 2008), and the result is shown in FIGS. 2 and 3.

Experimental Procedures

By using the ligature induced periodontal disease model, periodontal disease was induced by tying left upper second molar tooth of male rat (7 weeks, Samtaco Biokorea) after anesthetizing systemically by intraperitoneal injection of a mixed solution of ketamin at 200 mg/kg and xylazine at 20 mg/kg. The test drug at daily dose of 200 mg/kg and 400 mg/kg was orally administered. As the rat was anesthetized by carbon dioxide, the upper maxillary containing the tooth and fixed with 10% neutral buffered formalin to observe the tissue.

Image analysis was performed by obtaining 3-D image of the tissue with Amira$^R$ software (Konarad-Zuse-Zentrum fur Informationstechnik Berlin, Germany) by using animal CT (Micro cat II, Simense, USA). The effect of suppressing alveolar bone absorption was confirmed by measuring the distance between alveolar bone crest (AC) and cemento-enamel junction (CEJ) with image analysis program.

Experimental Results

As shown in FIGS. 2 and 3, the combined extract of Preparation Example 5 suppressed the alveolar bone absorption in periodontal disease animal model.

Experimental Example 5

Efficacy of Bone Regeneration in Animal Model

Figure 4:
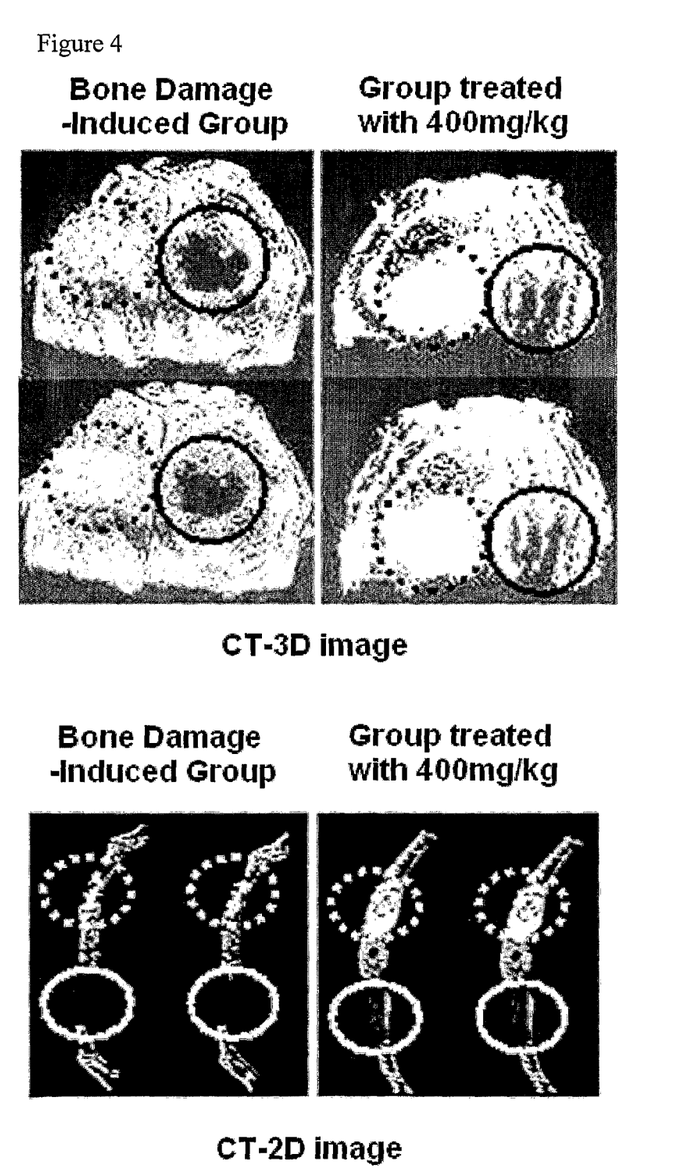
FIG. 4 is a CT image showing the activity of promoting the bone regeneration in an animal model with artificial bone damage for the combined extract of the Preparation Example 5 (circle with dotted line indicates the region coated with beta-TCP after bone damage, and circle with solid line indicates the region with bone damage only).
Figure 5:
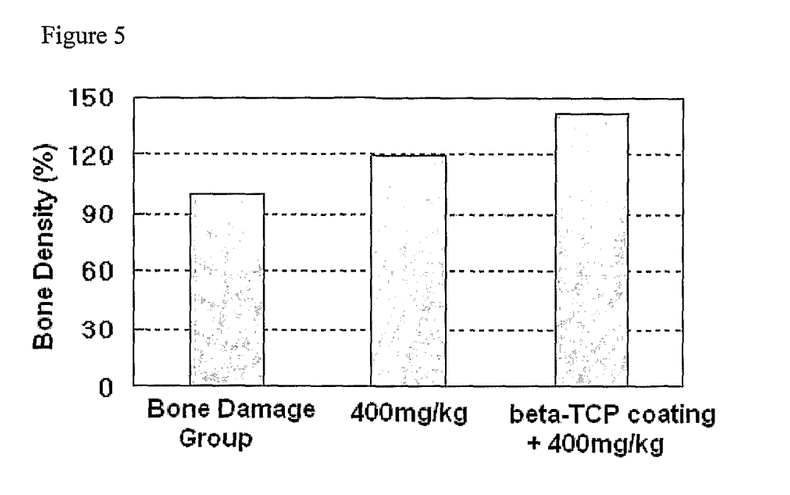
FIG. 5 is a graph showing the activity of promoting the bone regeneration in an animal model with artificial bone damage for the combined extract of the Preparation Example 5 (percentile of the bone density for the induced group).

In order to measure the efficacy of bone regeneration in animal model for the combined extract in Preparation Example 5, evaluation was made by using the method of Schmid J et al. (Schmid J et al., Clin. Oral Implants Res. 8, 75-81, 1997), and the result is shown in FIGS. 4 and 5.

Experimental Procedures

To use rabbit skull which has a similar pattern to alveolar bone, cortical bone was removed at right and left regions in 8 mm circles after anesthetizing systemically by intraperitoneal injection of a mixed solution of ketamin at 200 mg/kg and xylazine at 20 mg/kg. One was lest without the bone and the other was applied with beta-TCP (beta-tricalcium phosphate, Dentium, Korea), bone regeneration inducing agent, and stabilized for 3 days. Test drugs were administered orally for 1 week at daily dose of 400 mg/kg, and the rabbit were anesthetized with carbon dioxide to remove the bone defect site. The tissue was fixed with 10% neutral buffered formalin to observe the tissue.

Image analysis was performed by obtaining 3-D image of the tissue with Amira$^R$ software (Konarad-Zuse-Zentrum fur Informationstechnik Berlin, Germany) by using animal CT (Micro cat II, Simense, USA). Bone regeneration was confirmed by measuring the bone density with image analysis program.

Experimental Results

As shown in FIGS. 4 and 5, the combined extract of Preparation Example 5 promotes bone regeneration in the defect site.

With the above examples, the extract according to the present invention has an effect in the prevention and treatment of periodontal disease accompanying alveolar bone regeneration in osteoblast proligeration test, anti-inflammation test, ligature-induced periodontal disease model test and rabbit calvarial defect-induced bone regeneration model test.

Example 4

Preparation of Tablets

The above herbal extract 100 mg, light anhydrous silicic acid 5 mg, magnesium stearate 2 mg, amorphous cellulose 25 mg, sodium starch glycolate 13 mg, corn starch 50 mg and suitable amount of anhydrous ethanol was mixed and formed into tablets by using conventional method.

Example 5

Preparation of Health Food

| | |
|---|---|
| Above herbal medicine extract | 1000 mg |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinamide | 1.7 mg |
| Folic acid | 50 μg |
| Calcium Pantothenate | 0.5 mg |
| Mineral mixture | suitable amount |
| Ferrous sulfate | 1.75 mg |
| Zinc oxide | 0.82 mg |
| Magnesium carbonate | 25.3 mg |
| Monopotassium phosphate | 15 mg |
| Dipotassium phosphate | 55 mg |
| Potassium citrate | 90 mg |
| Calcium carbonate | 100 mg |
| Magnesium chloride | 24.8 mg |

The above ratios of vitamins and mineral mixture illustrate a preferable example of mixing ingredients relatively suitable for health food; however, the ratios can be modified. And, the above ingredients can be mixed according to a common health food preparation method, and then, made into a granule, and used for preparation of a health food composition by common method.

Example 6

Preparation of Health Beverage

| | |
|---|---|
| Above herbal medicine extract | 1000 mg |
| Citric acid | 1000 mg |
| Oligosaccharide | 100 g |
| Japanese apricot concentrate | 2 g |
| Taurin | 1 g |
| Purified water added so as to reach a total amount of | 900 mL |

The above ingredients were mixed according to a common health beverage preparation method, and heated with agitation at 85° C. for about 1 hour, and then, the prepared solution was filtered to collect in a sterilized 2 L vessel, seal sterilized and refrigeration stored.

The above ratios illustrate a preferable example of mixing ingredients relatively suitable for a favorite beverage; however, it can be modified according to regional and ethnic taste such as a demand class, a demand country, use, etc.

The invention claimed is:

1. A method for treating a periodontal disease in a human in need thereof consisting essentially of administering therapeutically effective amounts of an extract of *Coptidis Rhizoma* and *Pharbutidis Semen* to said human in need thereof to treat the periodontal disease.

2. The method according to claim 1, wherein a weight ratio of *Coptidis Rhizoma* to *Pharbutidis Semen* in the extract is from 1:1 to 25:1 in dry matter weight.

3. The method according to claim 2, wherein the weight ratio of *Coptidis Rhizoma* to *Pharbutidis Semen* in the extract is from 2.5:1 to 20:1 in dry matter weight.

4. The method according to claim 1, wherein the extract is a crude extract obtained with one or more solvents selected from the group consisting of water, a straight alcohol with the number of carbon atoms ranging from 1 to 4, and a branched alcohol with the number of carbon atoms ranging from 1 to 4.

5. The method of claim 1, wherein the extract is a solvent-soluble extract obtained by adding at least one aqueous solution of a straight alcohol with the number of carbon atoms ranging from 1 to 6 or a branched alcohol with the number of carbon atoms ranging from 1 to 6 to a crude extract obtained with one or more solvents selected from the group consisting of water, a straight alcohol with the number of carbon atoms ranging from 1 to 4, and a branched alcohol with the number of carbon atoms ranging from 1 to 4.

6. The method according to claim 1, wherein the periodontal disease is selected from the group consisting of stomatitis, gingivitis, periodontitis, alveolar bone damage, alveolar osteoporosis, alveolar osteomalacia, alveolar bone loss and alveolar Osteochondrodysplasia.

7. The method according to claim 1, wherein the extract is administered in an amount of 0.1 to 500 mg of extract/kg of said human per day.

* * * * *